United States Patent [19]

Sindo et al.

[11] 4,260,580
[45] Apr. 7, 1981

[54] CLINICAL ANALYZER

[75] Inventors: Isao Sindo; Yoshio Matsuoka, both of Katsuta; Kasumi Yoshida, Mito, all of Japan

[73] Assignee: Hitachi, Ltd., Tokyo, Japan

[21] Appl. No.: 942,142

[22] Filed: Sep. 14, 1978

[30] Foreign Application Priority Data

Sep. 14, 1977 [JP] Japan .................................. 52-111050

[51] Int. Cl.³ .............................................. G01N 1/14
[52] U.S. Cl. ..................................... 422/64; 364/497; 422/65; 422/67
[58] Field of Search ....................... 422/63, 64, 65, 66, 422/67; 364/497

[56] References Cited

U.S. PATENT DOCUMENTS

| | | | |
|---|---|---|---|
| 3,960,497 | 6/1976 | Acord | 422/67 |
| 4,058,367 | 11/1977 | Gilford | 422/67 |
| 4,113,436 | 9/1978 | Werder et al. | 422/67 |
| 4,166,095 | 8/1979 | Kling et al. | 422/67 |

*Primary Examiner*—R. E. Serwin
*Attorney, Agent, or Firm*—Craig and Antonelli

[57] ABSTRACT

Sample cups containing serum are removably loaded in a plurality of annular holders flexibly connected to make up a slidable chain which is moved through a limited path and passes a sampling position. Ion-selecting electrodes and a reference electrode are slightly spaced from the sampling position. A predetermined amount of serum in the sample cup that has arrived at the sampling position is distributed to a measurement tank. The electromotive force based on the ion to be measured is detected, and the ion concentration is printed out on a printer on the basis of the detection result. Normally, samples sequentially arriving at the sampling position are distributed to the measurement tank for continual analysis. Upon receipt of an emergency sample, an interruption switch on the operation panel is depressed for transmitting an interruption measurement command to a control section. After completion of the ongoing measurement of an ordinary sample, the chain motion is stopped with the particular sample kept at the sampling position, which sample is replaced manually by the emergency sample. A wide open sapce is provided around the sampling position to facilitate sample cup removal from and insertion into the holder. Depressing the start switch with the emergency sample at the sampling position, only the emergency sample is analyzed, after which the analyzer is stopped again. The interruption measurement command is cancelled by the interruption switch and the start switch is turned on, thus restarting continual measurement of ordinary samples.

8 Claims, 5 Drawing Figures

CLINICAL ANALYZER

BACKGROUND OF THE INVENTION

1. Field of the Invention

This invention relates to a clinical analyzer suitably used for clinical inspection, or more in particular to a clinical analyzer for continually measuring the items of analysis contained in a living body fluid by discrete process.

2. Description of the Prior Art

Typical analyzers to which the present invention is applicable include those in which a plurality of samples are transferred from sample containers to another type of liquid containers, and after being subjected to a chemical reaction, measured in the containers or moved together with the containers to another position for measurement, and those in which the samples are measured without special reaction. For convenience's sake, the analyzer of the latter type will be explained below.

In an automatic analyzer, a multiplicity of samples are usually arranged so that components to be inspected are measured continually. Considerable length of time is required before the prearranged samples are all completely measured. Nonetheless, the inspection laboratory of hospitals or like is often required to conduct an emergency inspection of a patient's blood for urgent necessity of operation or like. This is especially the case with ion components of such elements as sodium, potassium, calcium and chlorine. Therefore, a function to enable emergency measurement by interruption in the process of ordinary measurement of samples on the automatic analyzer will greatly reduced the complexity which otherwise might be encountered in the inspection work.

The conventional automatic analyzers, however, are such that even an emergency sample is also required to be set ordinarily in the sample transfer system for transfer to the component detecting position, and therefore are not suitable for emergency inspection.

SUMMARY OF THE INVENTION

Accordingly, it is the primary object of the present invention to provide a clinical analyzer in which although ordinary samples are continually measured automatically, a sample requiring emergency inspection is capable of interrupting them and being immediately measured.

Another object of the invention is to provide a clinical analyzer in which even in the case of interruption by the sample requiring emergency inspection, the order of arrangement of ordinary samples is not disturbed.

Still another object of the present invention is to provide a clinical analyzer in which the results of measurement of the emergency sample are obtainable within a short period of time by simple operation.

According to the present invention, there is provided a clinical analyzer in which a predetermined quantity of sample of living body liquid in a sample container is transferred from the sampling position to another container and then measurement is conducted on the analysis items of the transferred sample. Ordinary samples are moved in such a manner as to pass the sampling position sequentially and therefore continually measured in the order of arrival at the sampling position. In the case where emergency measurement is required, an interruption measurement command is transmitted to a control section by an interruption switch. In compliance with the interruption measurement command, the movement of the container chain of the ordinary samples is stopped upon completion of the measurement of an ordinary sample already in the sampling position. In the sampling position, the emergency sample is placed and analyzed. The sampling position is located in a broad and open environment to facilitate exchange of sample containers.

DESCRIPTION OF THE PREFERRED EMBODIMENTS

An analyzer according to a preferred embodiment of the present invention comprises a sampler for sequentially and intermittently transporting at regular intervals of time a chain of sample containers loaded in annular holders, to a sampling position, a sample transfer device for absorbing a predetermined amount of sample into a suction tube at the sampling position, diluting it with a predetermined amount of reagent and transferring the resulting solution to another sample container, a measuring device for quantifying the substance of the transferred sample by detecting the physical and chemical properties thereof, and an indicator including a printer or like for printing out the measurement result. In order to perform interruption by an emergency sample or specimen in preference to ordinary samples loaded in the sampler for sequential measurement, the analyzer according to the invention further comprises emergency interruption command means by which the sampler is stopped temporarily, the emergency sample is sampled and measured, the result of measurement thereof is printed out separately from the ordinary samples, and the sampler operation is restored for measurement of the general samples. For this purpose, the ordinary sample already measured is removed and replaced by the sample requiring emergency inspection is inserted at the sampling position, and the measuring operation is performed.

In a preferred embodiment of the present invention, a flexible chain is used as the holder of the sample containers, and may be replaced with equal effect by a turn table or like.

When the analyzer is not in analyzing operation, the sample suction tube of the sample transfer device for transferring the living body fluid sample from the sampling position to another container is kept stationary at a position upward of the container or between the sampling position and another container in order to avoid interference with the exchange of the sample containers at the sampling position.

An embodiment of the present invention will be described below with reference to the drawings. First, a schematic configuration of the embodiment will be explained with reference to FIGS. 1 to 4.

Figure 1:
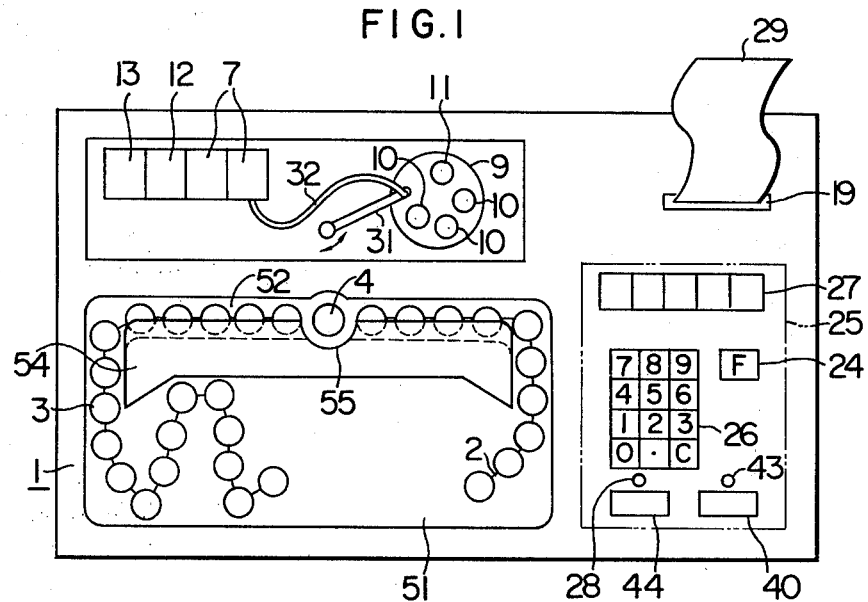
FIG. 1 is a plan view schematically showing an ion analyzer according to an embodiment of the present invention.

The embodiment of FIG. 1 is an application of the present invention to the ion analyzer. An operation panel 25 carries a function key and a ten key for entering analysis conditions, range of normal values, print format and like, a display lamp 27 for indicating data, an interruption switch 40, an interruption demand lamp 43, a measurement start switch 44 and a start indication lamp 28. A printer 19 for recording the results of measurement indicates on a printing paper 29 such information as the sample number, whether or not a normal value is involved, presence or absence of error, and identification of emergency or normal measurement.

Figure 2:
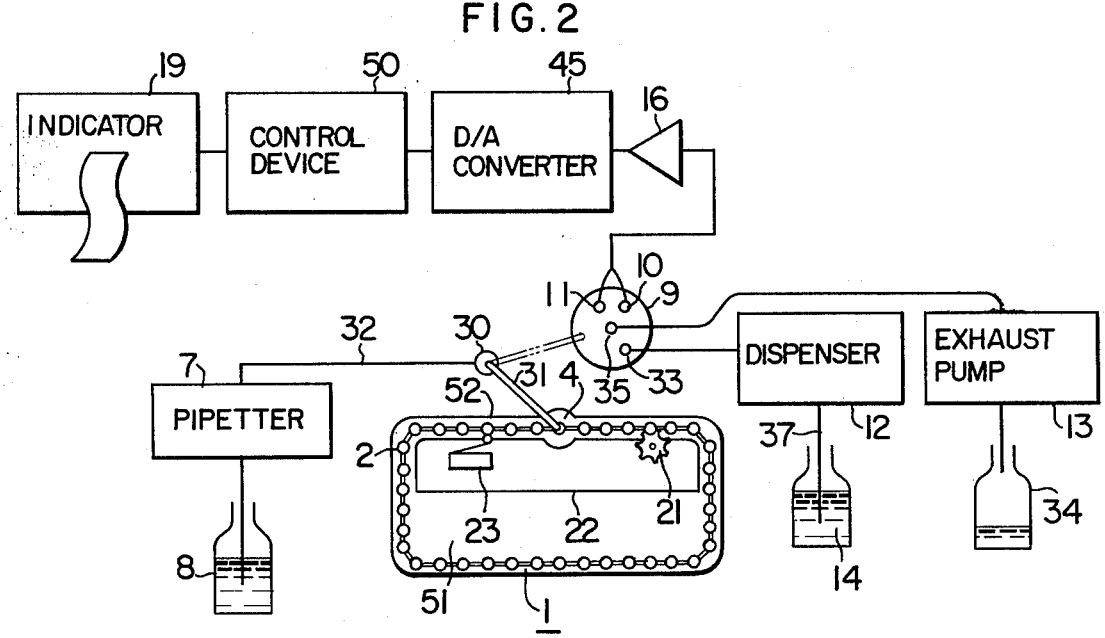
FIGS. 2 and 3 are diagrams for explaining the function of the embodiment shown in FIG. 1.

A sample chain 2 is comprises of a multiplicity of flexibly-connected annular holders, at the upper part of each of which a cylindrical sample cup is adapted to be inserted or taken out. The sampler 1 has a tray 51 which is adapted to carry the sample chain 2 mounted with the multiplicity of sample cups 3. As shown in FIG. 2, the sampler 1 comprises a driving section including a sprocket 21 for transporting the sample chain 2, a chain guide member 22 and a detector 23 for reading the data on the samples. The chain 2 is what is called a snake chain flexibly constructed so as to mount the sample cups 3 of appropriate containers such as test tubes. The chain 2 is driven in one direction in such a manner that the sample cups 3 are moved sequentially and intermittently to a specified position, i.e., the sampling position or station 4. The sampling position 4 is located midway of the limited path 52 for transferring the chain of the sample cups 3. Around the sampling position 4, an open space is provided large enough to allow insertion of fingers in order to facilitate removal of the sample cup 3 from the chain 2 and the loading of another sample cup. As shown in FIG. 2, such an open space is comprised of a recess formed in the guide member 22, thereby partially widening the limited path 52. A cover 54 is mounted on the guide member 22 to cover a part of the limited path 52. The cover 54 makes it impossible to take out most of the sample cups 3 in the limited path, although a large cutout 55 formed in that part of the cover 54 corresponding to the sampling position 4 facilitates exchange of the sample cup.

Figure 3:
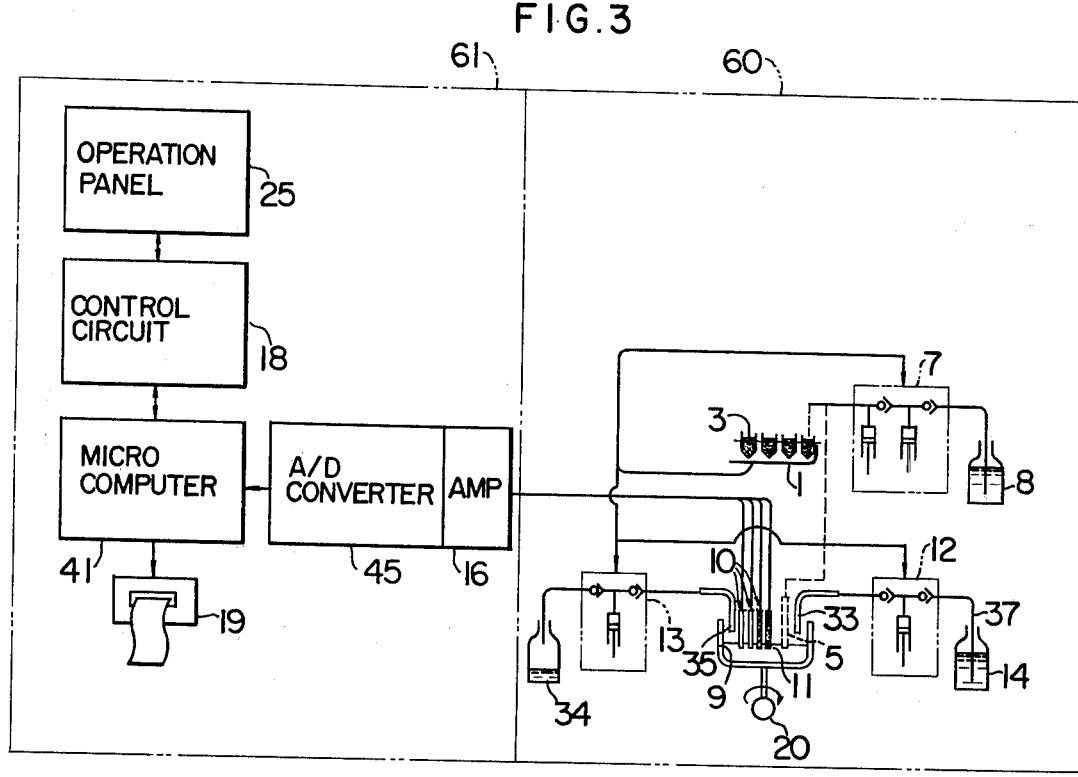
Figure 4:
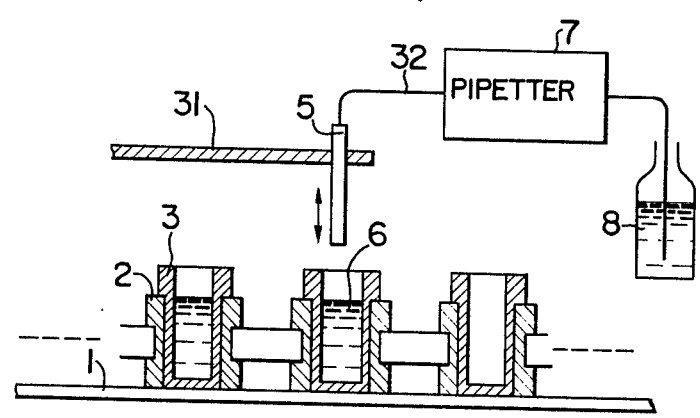
FIG. 4 is a diagram for explaining the general construction around the sampling position of the embodiment shown in FIG. 1.

The ion analyzer is roughly divided into an analysis section 60 and a data processing section 61 as shown in FIG. 3. The data processing section 61 includes an amplifier 16, an analog-to-digital converter 45, a microcomputer or central processing unit 41, a control circuit 18, an operation panel 25 and an indicator 19. The control circuit 18, the microcomputer 41, the operation section and the memory are collectively called the control device 50.

The measuring tank 9 may take various forms. In one form, it is fixed. In another form, the containers may be rotated. In still another form, containers may be replaced with other liquid-filled containers together with respective samples. The embodiment under consideration employs the measuring tank 9 rotatable within a predetermined position. A distributor 30 includes what is called pipetter 7 having a syringe mechanism and a movable arm 31. The pipetter 7 includes a suction-discharge mechanism for sucking and discharging the diluted solution in the diluted solution tank 8 and a sample suction tube 5 for sucking and discharging the sample liquid. The sample suction tube 5 is mounted at the forward end of the movable arm 31 and connected to the pipetter 7 by a flexible tube 32. The sample suction tube 5 is movable vertically by the movable arm 31 between the sampling position 4 on the sampler 1 and the measuring tank 9.

Within the measuring tank 9, a plurality of ion-selecting electrodes 10 for sodium, potassium, chlorine or like and a reference electrode 11 are arranged in such a manner as to be immersed in the sample when the particular sample is placed in the measuring tank 9. The suction tube 37 of the dispenser 12 having the tube 33 is inserted in the reference liquid tank 14 filled with a calibrating reference liquid containing ions of predetermined concentration. The tube 33 extends into the liquid container 9. The tube 35 connected to the exhaust pump 13 is opened to the bottom of the measuring tank 9 for exhausting the liquid into the liquid exhaust tank 34 after measurement and cleaning.

Assume that the sample cut 3 containing the serum sample 6 is loaded on the chain 2 and set on the sampler 1. In response to the measurement start command applied from the measurement start switch 44 to the control device 50, the sprocket 21 is set in motion so that the chain 2 is driven, thereby transferring the sample to the sampling position 4. At the same time, the dispenser 12 is actuated and supplies the reference liquid into the measuring tank 9 from the reference liquid tank 14, thus cleaning the internal part of the measuring tank 9 with the reference liquid. After the measuring tank 9 is cleaned, the liquid exhaust pump 13 is driven so that the liquid is exhausted and the reference liquid is again introduced into the measuring tank 9 from the tank 14. With the electrodes 10 and 11 immersed in the liquid, the measuring tank 9 is rotated by the rotation drive source 20 while at the same time measuring the ion concentration, and the resulting measurement is stored in the control device 50.

Next, the measuring tank 9 is emptied by the liquid exhaust pump 13. The distributor 30 is actuated thereby to lower the sample suction tube 5. The pipetter 7 is actuated, thus sucking and holding a predetermined amount of sample and diluted liquid. The sample suction tube 5 is moved by the distributor 30 to the position of the measuring tank 9 where the sample liquid is discharged into the measuring tank 9. The concentrations of Na, K and Cl ions in the sample, are measured and the difference between the measurement value and the value based on the reference liquid is calculated to determine the ion concentration of the sample. The ion concentration thus determined, together with the sample number, is printed out on the indicator 19. Thus a measuring cycle including transportation, pick-up, transfer, measurement, calculation and printing of the result of inspection of a sample is completed. This is followed by the moving of the sample chain 2 for carrying out a similar measuring cycle, so that a plurality of samples arranged in predetermined sequence are automatically measured in succession. The foregoing is the description of a general method of continual measurement of a series of arranged samples.

An emergency sample is measured in the manner mentioned below. When an emergency interruption measurement command is applied to the control device 50, the analyzer operation is suspended after inspection of the ordinary sample being measured. The sample stationary at the sampling position 4 is the last sample measured. This sample is taken out of the holder of the sample chain 2 and, in its place the container having the emergency sample therein is inserted into the holder. A measuring command is issued to the control device 50. As described above, the preceding sample is exhausted from the measuring tank 9, a reference liquid is supplied into the measuring tank 9 through the dispenser 12 thereby to clean the measuring tank 9, the reference liquid is exhausted by the exhaust pump 13, and the reference liquid is again supplied into the measuring tank 9 by the dispenser 12. With the ion-selecting electrodes 10 and the reference electrode 11 immersed in the liquid, the measuring tank 9 is rotated by the rotation drive source 20 at such a speed that the liquid fails to jump out. In the process, the ion concentration of the reference liquid is measured, after which the reference liquid is exhausted. The emergency specimen placed at the sampling position 4 is picked up by the pipetter 7, the distributor 30 is actuated, the sample is exhausted into the measuring tank 9, and the ion concentration thereof is measured. From the difference between the measurement of the reference liquid and that of the emergency specimen, the concentration of the sample is determined and applied to the indicator 19 while at the same time being displayed by the indication lamp 27, thus completing the analysis of the emergency sample.

The emergency sample thus measurable is not limited to one in number but any number of such samples are capable of being measured in similar fashion by replacing the samples at the sampling positions. After measurement of the emergency sample, an emergency sample measurement release command is issued from the interruption switch 40 to the control device 50, thus terminating the state of emergency sample measurement. At the same time, the analyzer is restored to the original routine measurement for continuation of the ordinary measurement of specimens.

The routine measurement is executed by a program partially different from that of the emergency measurement. A program is selected by an interruption measurement signal and an interruption release signal. The sample chain is slided on the surface of the tray 51 with the sample containers loaded in the holders. The measuring tank 9 is generally so constructed that a plurality of ion-selecting electrodes are immersible at a time. The sampling position 4 may be constructed to accept a plurality of emergency samples at the same time.

Figure 5:
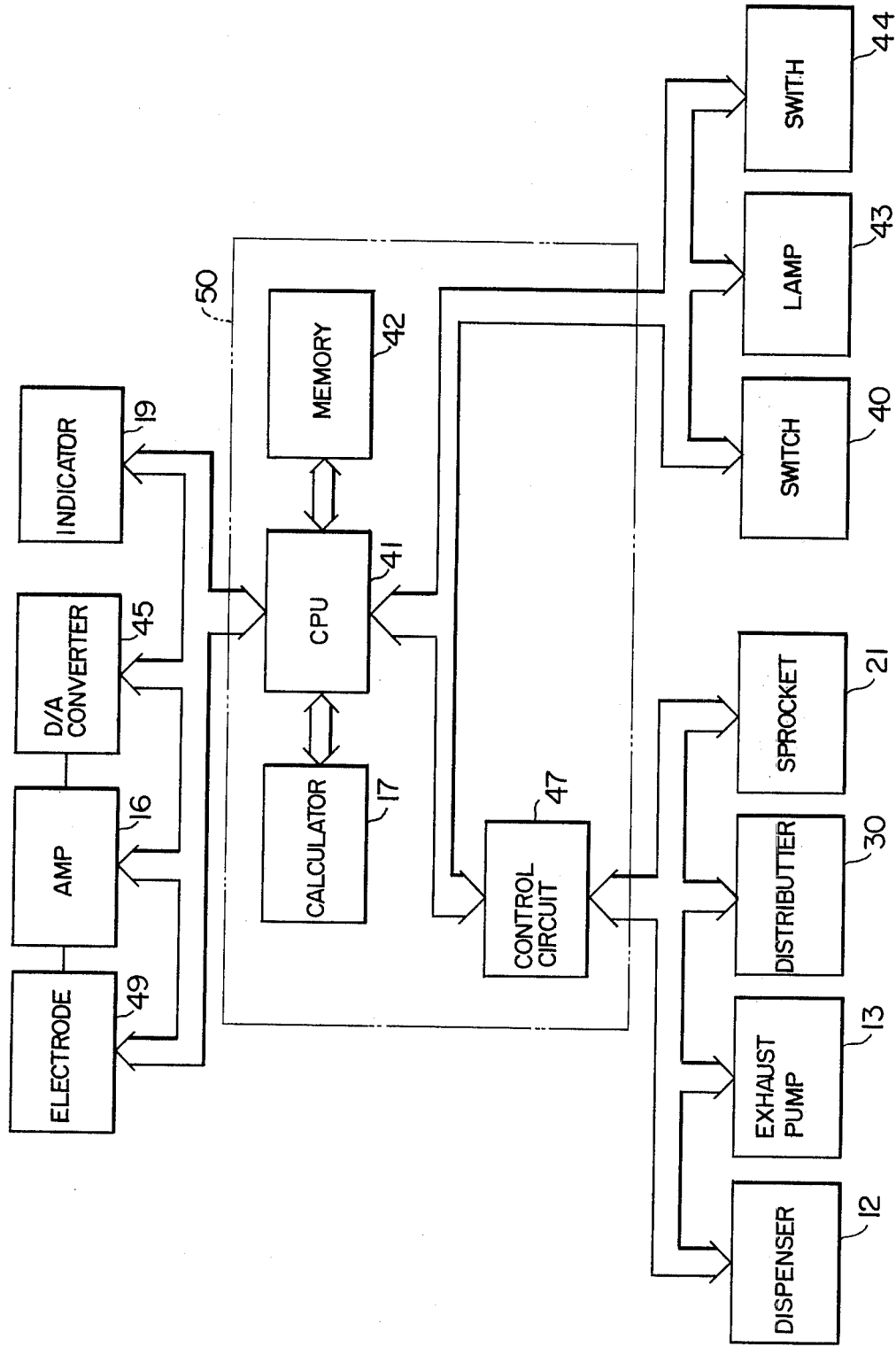
FIG. 5 is a diagram for explaining the command system of the embodiment shown in FIG. 1.

The control system of the above-mentioned embodiment will be explained more in detail below with reference to FIG. 5. For measuring an emergency sample by interruption of the process of routine measurement, the first requirement is to depress the interruption switch 40. At the press of the switch 40, the microcomputer or central processing unit 41 receives the interruption signal and stores it in the memory 42. At the same time, the interruption lamp 43 is lit, thereby informing the operator that an interruption demand is accepted. The analyzer measures the ordinary sample under inspection, and after printing out the resulting data on the printer 19, temporarily stops the operation thereof in compliance with the interruption demand. The sample at the sampling position 4 is already measured and therefore taken out. The interruption sample is inserted into the empty holder. Depressing the measurement start switch 44, the microcomputer 41 receives a signal from the switch 44 and instructs the exhaust pump 13 to exhaust the liquid out of the measuring tank 9. After the liquid is exhausted out of the measuring tank 9, the dispenser 12 is actuated, thus supplying the reference liquid from the reference liquid tank 14 into the measuring tank 9. The ions in the liquid are detected by the electrode system 49, and the detection signal is amplified by the amplifier 16. After that, the analog signal is converted into a digital signal by the analog-to-digital converter 45, and the resulting value is stored in the memory 42.

When the measurement start switch 44 is depressed, on the other hand, the control circuit 47, in response to the command from the microcomputer 41, actuates the distributor 30, lowers the sample suction tube 5, sucks and holds a predetermined amount of sample liquid in the suction tube 5, transfers the liquid to and discharges it into the measuring tank 9. As in the case of reference liquid, the output voltage associated with a specific component of the sample is measured by the electrode system 49. On the basis of the difference between the measurement of the reference liquid and that of the specific component, the calculating device 17 determines the ion concentration of the sample and applies the data to the printer 19. In this case, the interruption signal is stored in the memory 42 for the microcomputer 41. Therefore, the data printed out is affixed with a sample number with a symbol different from that for the routine measurement. Such a symbol may be in another form capable of discriminating the emergency measurement from the routine one.

Upon completion of the measurement of the interruption sample, the analyzer is suspended in operation according to the emergency measurement program. For measurement of another interruption sample, the preceding sample container at the sampling position 4 is removed and in place thereof, a container of the emergency sample to be measured is inserted into the holder, and then the measurement start switch 44 is depressed. In this way, any number of emergency samples can be measurable. For releasing the interrupted state and restoring the original routine measurement, the interruption switch 40 is depressed again, followed by the depressing of the measurement start switch 44. In response to the interruption release signal, the microcomputer 41 extinguishes the interruption demand lamp 43 while at the same time cancelling the interruption signal in the memory 42. Then the routine measurement is restarted in response to a measurement start signal.

We claim:
1. A clinical analyzer comprising
   (a) transport means for transporting a plurality of sample containers sequentially, each container containing a body fluid sample therein;
   (b) means for moving said transport means along a path in a direction to cause each sample container to pass a sampling position;
   (c) a sample receiving container arranged at a sample discharging position;
   (d) a pick-up means for taking out a predetermined amount of sample from the sample container moved to said sampling position and for discharging the taken-out sample into said sample receiving container;
   (e) a detector means for obtaining a measurement value according to an analyzing item of said sample retained in said sample receiving container;
   (f) means for indicating data on the basis of said measurement value;
   (g) a container exchanging means arranged along the moving path of said plurality of sample containers for permitting the exchange of a new sample container for one of the containers being transported by said transport means;
   (h) control means for controlling the operation of each of said means of said clinical analyzer whereby, in normal operation, the body fluid sam- ples in said sample containers are sequentially moved to the sampling position, sampled and measured for the analyzing item; said control means, in emergency operation, upon receipt of an interruption measurement command controlling the analyzer to measure only the sample in the sample container positioned in the container exchanging means and also stopping further movement of said plurality of sample containers and causing said pick-up means and said detector means to transfer a sample from a new sample container that has been manually exchanged for the sample container that has previously been sampled whereby the new sample is sampled and measured for an analyzing item and thereafter said control means in accordance with an interruption cancelling command returning the analyzer to normal operation; and (i) switching means for transmitting said interruption measurement command and said interruption cancelling command to said control means.

2. A clinical analyzer according to claim 1, in which said transport is a chain including a plurality of annular holders connected flexibly with each other, said chain being adapted to move intermittently through a limited path.

3. A clinical analyzer according to claim 2, in which said limited path is provided with a cover which is cut out at and in the neighbourhood of said sampling position.

4. A clinical analyzer according to claim 1, in which said pick-up means includes a sample suction tube movable between said sampling position and said sample discharging position, said sample suction tube being spaced from said sampling position while said container exchanging means is awaiting the exchange of the sample container.

5. A clinical analyzer according to claim 1, in which said indicating means comprises a printer, the measurement value of the sample measured during the emergency operation is printed out separately from the measurement values of the samples measured during normal operation.

6. A clinical analyzer according to claim 1, which further comprises means for rotating said receiving container at a speed such that the sample contained therein does not spill out, and wherein said detector means comprises at least one ion-selecting electrode extending in said sample receiving container.

7. A clinical analyzer according to claim 1, wherein said container exchanging means provides an open space where one of said sample containers may be taken out from said plurality of sample containers and a new sample container be inserted in place of the removed sample container, said open space being positioned so as to correspond to said sampling position and said container exchanging means including a member for preventing sample containers in front and to the rear of said sampling position from being taken out from said transport means.

8. A clinical analyzer comprising:
   (a) transport means for transporting a plurality of sample containers sequentially, each container containing a body fluid sample therein;
   (b) means for moving said transport means along a path in a direction to cause each sample container to pass a sampling position;
   (c) a sample receiving container arranged at a sample discharging position;
   (d) a pick-up means for taking out a predetermined amount of sample from the sample container moved to said sampling position and for discharging the taken-out sample into said sample receiving container;
   (e) means for introducing a reference liquid containing analysis items of known concentration into said sample receiving container;
   (f) means for detecting an electromotive force based on the reference liquid and/or body fluid sample in said sample receiving container;
   (g) means for discharging the reference liquid or body fluid sample from said sample receiving container;
   (h) calculator means for comparing the electromotive force based on said reference liquid with electromotive force based on said body fluid sample;
   (i) means for indicating data produced from said calculator means;
   (j) a container exchanger means provided above the moving path of the plurality of sample containers, said container exchanging means providing an open space where one sample container is taken out from the plurality of sample containers and in place thereof a new sample container is inserted, said open space being positioned to correspond to the sampling position and said container exchanging means providing a member for preventing the sample containers in front and rear of the sampling position from being taken out from the transport means;
   (k) control means for controlling the operation of each of said means of said clinical analyzer whereby, in normal operation, the body fluid samples in said sample containers are sequentially moved to the sampling position, sampled and measured for the analyzing item; said control means, in emergency operation, upon receipt of an interruption measurement command controlling the analyzer to measure only the sample in the sample container positioned in the container exchanging means and also stopping further movement of said plurality of sample containers and causing said pick-up means and said detector means to transfer a sample from a new sample container that has been manually exchanged for the sample container that has previously been sampled whereby the new sample is sampled and measured for an analyzing item and thereafter said control means in accordance with an interruption cancelling command returning the analyzer to normal operation; and
   (l) switching means for transmitting said interruption measurement command and said interruption cancelling command to said control means.

* * * * *